United States Patent [19]

Withers, Jr.

[11] Patent Number: 4,568,789

[45] Date of Patent: Feb. 4, 1986

[54] HYDROCARBON DEHYDROGENATION

[75] Inventor: Howard P. Withers, Jr., Pottstown, Pa.

[73] Assignee: Atlantic Richfield Company, Los Angeles, Calif.

[21] Appl. No.: 600,736

[22] Filed: Apr. 16, 1984

[51] Int. Cl.$^4$ ............................................. C07C 5/327
[52] U.S. Cl. ..................... 585/654; 585/656; 585/658; 585/660; 585/661; 585/444
[58] Field of Search .............. 585/654, 656, 658, 660, 585/661, 444; 208/135, 136, 138

[56] References Cited

U.S. PATENT DOCUMENTS

| | | | |
|---|---|---|---|
| 3,315,007 | 4/1967 | Abell et al. | 585/654 |
| 3,679,773 | 7/1972 | Kovach et al. | 585/654 |
| 3,682,838 | 8/1972 | Bloch | 585/661 |

FOREIGN PATENT DOCUMENTS 1397293  7/1973  United Kingdom ............... 585/654

Primary Examiner—William R. Dixon, Jr.
Assistant Examiner—Cynthia A. Prezlock
Attorney, Agent, or Firm—Craig E. Larson

[57] ABSTRACT

A method for dehydrogenating dehydrogenatable hydrocarbons which comprises contacting said hydrocarbon with an oxide of Ru having combined therewith an amount of alkali and/or alkaline earth metal which is sufficient to improve the selectivity to dehydrogenated hydrocarbon products. The oxide is reduced by the contact which is preferably carried at about 500° to 1000° C. Reducible oxides of Ru are regenerated by oxidizing the reduced composition wth oxygen. Bulk ruthenium oxides promoted by sodium and/or compounds thereof are particularly preferred contact solids.

22 Claims, No Drawings

HYDROCARBON DEHYDROGENATION

BACKGROUND OF THE INVENTION

This invention relates to dehydrogenation of dehydrogenatable hydrocarbons. This invention more particularly relates to oxidative dehydrogenation processes.

SUMMARY OF THE INVENTION

It has now been found that dehydrogenatable hydrocarbons may be dehydrogenated to hydrocarbon products by contacting a hydrocarbon-containing gas with a solid comprising: (1) a reducible oxide of ruthenium and (2) at least one member of the group consisting of alkali metals, alkaline earth metals, and compounds thereof. Alkali metals are selected from the group consisting of Li, Na, K, Rb and Cs. Alkaline earth metals are selected from the group consisting of Mg, Ca, Sr and Ba.

Dehydrogenatable hydrocarbons are desirably contacted with the solid at a temperature within the range of about 500° to 1000° C. The atomic ratio of ruthenium to alkali metal or alkaline earth metal is desirably within the range of about 1–500:1. The iron oxide is reduced by contact with the hydrocarbon and is reoxidizable by contact with an oxygen-containing gas.

Contacting dehydrogenatable hydrocarbons with oxides of Ru in the absence of an alkali metal or alkaline earth metal produces predominantly combustion products ($CO_x$). However, it has been found that incorporating an alkali metal or alkaline earth metal into the contact solid substantially reduces the formation of combustion products and improves dehydrogenated hydrocarbon product selectivity. It has further been found that bulk ruthenium oxides promoted with sodium give much improved activities and selectivities for hydrocarbon dehydrogenation conversion compared to supported ruthenium oxides promoted with sodium.

DETAILED DESCRIPTION OF THE INVENTION

Reducible oxides of Ru can be supplied from a variety of known sources. The term "reducible" is used to identify those oxides which are reduced by contact with hydrocarbon at temperatures within the range of about 500° to 1000° C. A preferred oxide is ruthenium dioxide.

The contact solid employed in the present process contains, in addition to a reducible oxide of Ru, at least one alkali metal or alkaline earth metal. Alkali metals are preferred. Sodium is particularly preferred. The amount of alkali/alkaline earth metal incorporated into the contact solid is not narrowly critical. The preferred atomic ratio of the reducible ruthenium oxide component (expressed as the metal, Ru) to the alkali/alkaline earth metal component (expressed as the metal, e.g., Na) is within the range of about 1–500:1, more preferably within the range of about 2–200:1, still more preferably within the range of about 2–10:1.

The contact solid may also contain other components commonly referred to as oxidative dehydrogenation agents (or catalysts). Oxidative dehydrogenation agents generally comprise at least one oxide of at least one metal, which oxides when contacted with dehydrogenatable hydrocarbons at dehydrogenation conditions (e.g., at a temperature selected within the range of about 500° to 1000° C.) produce dehydrogenated hydrocarbon products, coproduct water, and a reduced metal oxide. The composition thus contains at least one reducible oxide of at least one metal. The term 'reducible' is used to identify those oxides of metals which are reduced by contact with the hydrocarbons at dehydrogenation conditions (e.g., at temperatures selected within the range of about 500°–1000° C.). The term "oxide(s) of metal(s)" includes: (1) one or more metal oxides (i.e., compounds described by the general formula $M_xO_y$ wherein M is a metal and the subscripts $x$ and $y$ designate the relative atomic proportions of metal and oxygen in the composition) and/or (2) one or more oxygen-containing metal compounds, provided that such oxides and compounds have the capability of performing to produce dehydrogenated hydrocarbon products as set forth herein.

One class of preferred oxidative synthesizing agents comprises reducible oxides of metals selected from the group consisting of Mn, Sn, In, Ge, Sb, Pb, and Bi and mixtures thereof. Particularly effective oxidative dehydrogenation agents have been found to comprise a reducible oxide of manganese and mixtures of a reducible oxide of manganese with other oxidative dehydrogenation agents.

It is within the scope of the present invention to include other effective oxidative dehydrogenation agent components with the combined ruthenium oxide/alkali-alkaline earth metal system of the present invention. Thus, the ruthenium oxide/alkali-alkaline earth metal system may also contain a reducible oxide selected from the group consisting of Mn, Sn, In, Ge, Sb, Pb, Bi and mixtures thereof.

It is also within the scope of the present invention to include at least one phosphorus component in the solid. However, the contact solid of this invention is effective in the absence of phosphorus.

While the exact composition of the contact solids is more complex, the solids employed in the process of this invention may be described by the following empirical expression:

$$Ru_a\, B_b\, C_c\, P_d\, O_e$$

wherein B is selected from the group consisting of alkali and alkaline earth metals; C is selected from the group consisting of Mn, Sn, In, Ge, Pb, Sb, Bi and mixtures thereof; a, b, c, d and e indicate the atomic ratio of each component; and when a is 10, b is within the range of about 0.5–10, c is within the range of about 0–10, d is within the range of about 0–10, and e has a value which is determined by the valences and proportions of the other elements present.

These components may be associated with other support materials. However, in a presently preferred embodiment, a reducible oxide of Ru is employed as a support for the other components of the solids. While use of other supports is within the scope of this invention, it has been found that the use of bulk ruthenium oxides give superior results.

Accordingly, a particularly preferred embodiment of the present invention comprises contacting methane at a temperature within the range of about 500° to 1000° C. with a solid comprising a member of the group consisting of alkali metals and compounds thereof associated with a support comprising a reducible oxide of Ru. Preferably, the reducible oxide of Ru comprises ruthenium dioxide. Still more particularly, the presently preferred alkali metal associated with these supports is Na.

The contact solids employed in this invention can be prepared by any suitable method. Conventional methods such as precipitation, co-precipitation, impregnation, or dry-mixing can be used. Supported solids may be prepared by methods such as adsorption, impregnation, precipitation, co-precipitation, and dry-mixing. When phosphorus is incorporated in the agent, it is desirable to provide it in the form of a phosphate of an alkali metal or an alkaline earth metal. Substantially any compound of these elements can be employed in the preparation of the promoted synthesizing agent.

A suitable method of preparation is to impregnate a support with solutions of compounds of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solid is prepared for use by calcining, preferably in air, at a temperature selected within the range of about 300° to 1200° C. Particular calcination temperatures will vary depending upon the particular metal compound or compounds employed.

If phosphorus is used, the alkali/alkaline earth metal and phosphorus are preferably added to the composition as compounds containing both P and alkali/alkaline earth metals. Examples are the orthophosphates, metaphosphates, and pyrophosphates of alkali/alkaline earth metals. Pyrophosphates have been found to give desirable results. Sodium pyrophosphate is particularly preferred.

Regardless of how the components of the contact solid are combined, the resulting composite generally will be dried and calcined at elevated temperatures.

The dehydrogenatable hydrocarbon feedstock employed in the method of this invention is intended to include a wide variety of hydrocarbons: e.g., $C_2+$ alkanes, cycloalkanes, olefins, alkylaromatics, etc. The dehydrogenated product will of course depend in part on the feedstock selected. For example, alkanes may be dehydrogenated to form olefins, diolefins, alkynes, etc., and olefins may be dehydrogenated to form diolefins, alkynes, etc. Thus, potential uses for the present process include the following conversions:
(1) ethane→ethylene→acetylene;
(2) propane→propylene;
(3) butane→butene→butadiene;
(4) 2-methylbutane→2-methylbutenes→isoprene; and
(5) toluene→stilbene.

One preferred class of feedstocks comprises $C_2$–$C_5$ alkanes.

Operating temperatures for the contacting of hydrocarbon-containing gas and the ruthenium/alkali-alkaline earth metal solid are generally within the range of about 500° to 1000° C. If reducible oxides of metals such as In, Ge, or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds thereof) during methane contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Contacting dehydrogenatable hydrocarbons and the solid comprising a ruthenium oxide/alkali-alkaline earth metal composite to form dehydrogenated hydrocarbons also produces a reduced metal oxide and co-product water. The exact nature of the reduced metal oxides are unknown, and so are referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300° to 1200° C., the particular temperature selected depending on the metal(s) included in the solid.

In carrying out the present process, a single reactor apparatus containing a fixed bed of solids may be used with intermittent or pulsed flow of a first gas comprising dehydrogenatable hydrocarbons and a second gas comprising oxygen (e.g., oxygen, oxygen diluted with an inert gas, or air, preferably air). The hydrocarbon contacting step and the oxygen contacting step may also be performed in physically separate zones with solids recirculating between the two zones.

Thus, a suitable method of dehydrogenating dehydrogenatable hydrocarbons comprises: (a) contacting a gas comprising said hydrocarbons and particles comprising a reducible Ru oxide/alkali-alkaline earth metal composite to form dehydrogenated hydrocarbon products, co-product water, and reduced metal oxide; (b) removing particles comprising reduced metal oxide from the first zone and contacting the reduced particles in a second zone with an oxygen-containing gas to form particles comprising a reducible Ru oxide/alkali-alkaline earth metal composite; and (c) returning the particles produced in the second zone to the first zone. The steps are preferably repeated at least periodically, and more preferably the steps are continuous. In the more preferred embodiment solids are continuously circulated between at least one hydrocarbon-contact zone and at least one oxygen-contact zone.

Particles comprising a reducible Ru oxide/alkali alkaline earth metal composite which are contacted with hydrocarbon may be maintained as fluidized, ebullating, or entrained beds of solids. Preferably the hydrocarbon is contacted with a fluidized bed of solids.

Similarly, particles comprising reduced metal oxide which are contacted with oxygen may be maintained as fluidized, ebullating or entrained beds of solids. Preferably oxygen is contacted with a fluidized bed of solids.

In one more preferred embodiment of the present invention, hydrocarbon feedstock and particles comprising a promoted oxidative dehydrogenation agent are continuously introduced into a hydrocarbon contact zone maintained at dehydrogenation conditions. Gaseous reaction products from the methane contact zone (separated from entrained solids) are further processed—e.g., they are passed through a fractionating system wherein the desired hydrocarbon products are separated from unconverted hydrocarbon and combustion products. Unconverted hydrocarbon may be recovered and recycled to the hydrocarbon contact zone.

Particles comprising reduced metal oxide are contacted with oxygen in an oxygen contact zone for a time sufficient to oxidize at least a portion of the reduced oxide to produce a reducible metal oxide and to remove, i.e., combust, at least a portion of any carbonaceous deposit which may form on the particles in the hydrocarbon contact zone. The conditions of the oxygen contact zone will preferably include a temperature selected within the range of about 300° to 1200° C., pressures of up to about 30 atmospheres, and average particle contact time within the range of about 1 to 120 minutes. Sufficient oxygen is preferably provided to oxidize all reduced metal oxide to produce a reducible oxide and to completely combust any carbonaceous deposit material deposited on the particles. At least a portion of the particles comprising promoted oxidative dehydrogenation agent which are produced in the oxygen contact zone are returned to the hydrocarbon contact zone.

The rate of solids withdrawal from the hydrocarbon contact zone is desirably balanced with the rate of solids passing from the oxygen contact zone to the hydrocarbon contact zone so as to maintain a substantially constant inventory of particles in the hydrocarbon contact zone, thereby enabling steady state operation of the dehydrogenation system.

What is claimed is:

1. A method for dehydrogenating $C_2+$ alkanes which comprises producing the corresponding olefins and co-product water by contacting at a temperature within the range of about 500°–1000° C. a gas comprising said alkanes and a solid comprising:
    (a) a reducible oxide of Ru and
    (b) at least one member selected from the group consisting of alkali metals, alkaline earth metals, and compounds thereof.

2. The method of claim 1 wherein component (b) of said solid is selected from the group consisting of alkali metals and compounds thereof.

3. The method of claim 2 wherein the alkali metal is selected from the group consisting of Li, Na, K, Rb, Cs, and compounds thereof.

4. The method of claim 2 wherein the alkali metal is selected from the group consisting of sodium, sodium compounds and mixtures thereof.

5. The method of claim 1 wherein the said reducible oxide and the alkali/alkaline earth metal are associated with a support material.

6. The method of claim 5 wherein said reducible oxide is provided as a support for at least one of the other components of said solid.

7. The method of claim 1 wherein the solid is prepared from ruthenium dioxide.

8. The method of claim 1 wherein the atomic ratio of Ru to alkali/alkaline earth metal in said solid is within the range of about 1–500:1.

9. The method of claim 1 wherein the atomic ratio of Ru to alkali/alkaline earth metal in said solid is within the range of about 2–100:1.

10. The method of claim 1 wherein the said solid is described by the empirical formula:

$$Ru_a B_b C_c P_d O_e$$

wherein B is selected from the group consisting of alkali metals, alkaline earth metals, and mixtures thereof; C is selected from the group consisting of Mn, Sn, In, Ge, Pb, Sb, Bi and mixtures thereof; a, b, c, d, and e indicate the atomic ratio of each component; and when a is 10, b is within the range of about 0.5–10, c is within the range of about 0–10, d is within the range of about 0–10, and e has a value which is determined by the valences and proportions of the other elements present.

11. The method of claim 10 wherein the components are associated with a support material.

12. The method of claim 11 wherein a reducible oxide or Ru is provided as a support for the other components of said solid.

13. The method of claim 12 wherein C is Mn.

14. The method of claim 13 wherein B is Na.

15. The method of claim 13 wherein B is K.

16. The method of claim 13 wherein B is Li.

17. A method for dehydrogenating $C_2+$ alkanes to form the corresponding olefins which comprises:
    (a) contacting at a temperature within the range of about 500°–1000° C. a gas comprising said alkanes and a solid comprising:
        (1) a reducible oxide of Ru and (2) at least one member selected from the group consisting of alkali metals, alkaline earth metals, and compounds thereof, said contacting producing olefins, coproduct water and solids comprising a reduced Ru oxide;
    (b) recovering olefins;
    (c) at least periodically contacting the solids comprising reduced Ru oxide with an oxygen-containing gas to produce a solid comprising a reducible Ru oxide;
    (d) contacting the solids produced in step (c) as recited in step (a).

18. The method of claim 17 wherein the said solid of step (a) comprises an alkali metal or compound thereof.

19. The method of claim 18 wherein the said solid of step (a) comprises an alkali metal or compound thereof on a support consisting essentially of said reducible Ru oxide.

20. The method of claim 17 wherein the temperature of step (c) is within the range of about 300° to 1200° C.

21. The method of claim 1 wherein said alkanes comprise $C_2$–$C_5$ alkanes.

22. The method of claim 17 wherein said alkanes comprise $C_2$–$C_5$ alkanes.

* * * * *

UNITED STATES PATENT AND TRADEMARK OFFICE
CERTIFICATE OF CORRECTION

PATENT NO. : 4,568,789
DATED : February 4, 1986
INVENTOR(S) : Howard P. Withers, Jr.

It is certified that error appears in the above-identified patent and that said Letters Patent is hereby corrected as shown below:

Claim 12, line 2:

"or" should read -- of --

Signed and Sealed this

Thirteenth Day of May 1986

[SEAL]

Attest:

DONALD J. QUIGG

Attesting Officer    Commissioner of Patents and Trademarks